United States Patent [19]

Stephens et al.

[11] Patent Number: 4,534,941
[45] Date of Patent: Aug. 13, 1985

[54] ANALYTICAL INSTRUMENT THERMOELECTRIC TEMPERATURE REGULATOR

[75] Inventors: Donald E. Stephens, Palo Alto; Robert J. Ehret, Los Altos, both of Calif.

[73] Assignee: Beckman Instruments, Inc., Fullerton, Calif.

[21] Appl. No.: 327,372

[22] Filed: Dec. 4, 1981

[51] Int. Cl.³ .............................................. G01N 31/08
[52] U.S. Cl. ........................................ 422/70; 422/109
[58] Field of Search ................... 422/70, 109; 436/161; 73/23.1

[56] References Cited

U.S. PATENT DOCUMENTS

| | | | |
|---|---|---|---|
| 3,431,077 | 3/1969 | Danforth | 23/253 |
| 3,592,046 | 7/1971 | Cramers et al. | 73/23.1 |
| 3,806,321 | 4/1974 | Durrum et al. | 23/253 R |
| 4,044,593 | 8/1977 | Haruki et al. | 73/23.1 |
| 4,057,998 | 11/1977 | Moreaux | 73/23.1 |
| 4,088,458 | 5/1978 | Jourdan | 55/197 |

FOREIGN PATENT DOCUMENTS 1204897 9/1970 United Kingdom .

OTHER PUBLICATIONS

Hackh's Chemical Dictionary, p. 673, 4th Ed., McGraw Hill, N.Y., 1969.
LKB4400—The Benefits, Durrum Amino Acid Analyzer, Model D-500.
Biotronik Amino Acid Analyser LC 7000, Chromaspek Instrument by Rank-Hilger.

Primary Examiner—Hiram H. Bernstein
Attorney, Agent, or Firm—W. H. May; P. R. Harder

[57] ABSTRACT

A temperature control system used to precisely and accurately control the temperature of a fluid stream in an analytical system designed for investigation of the chemical constituents of the fluid stream. One example of use is in chromatography such as for the chromatographic column in an amino acid analyzer system. The temperature control system utilizes a set of thermoelectric modules to transfer heat between a thermoconductive block which holds the chromatographic column and an air exchange heat sink which obtains heat from or disposes heat into ambient air as required. The control system regulates the temperature at a very rapid rate in order to minimize the recycle time of the instrument.

9 Claims, 7 Drawing Figures

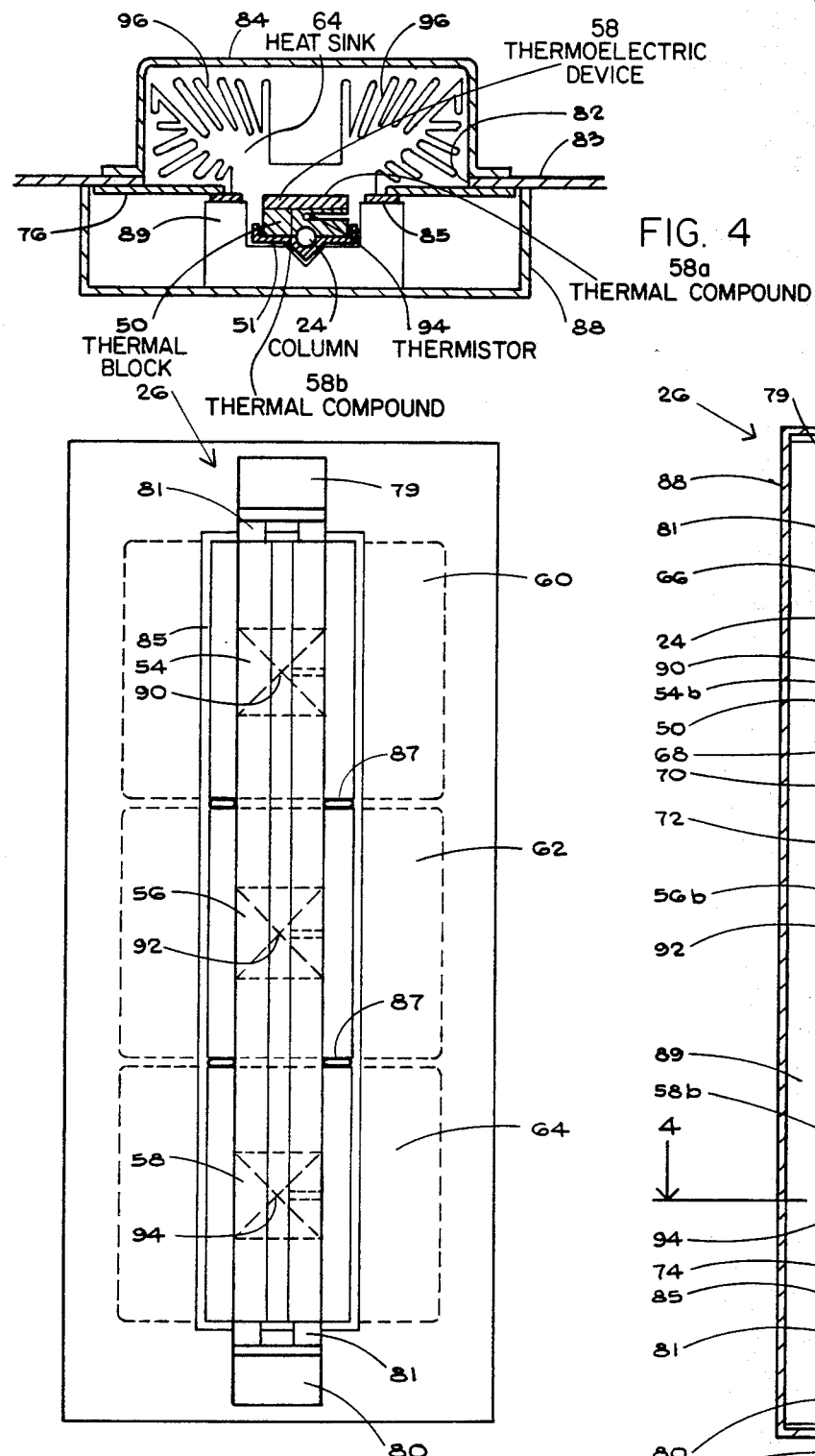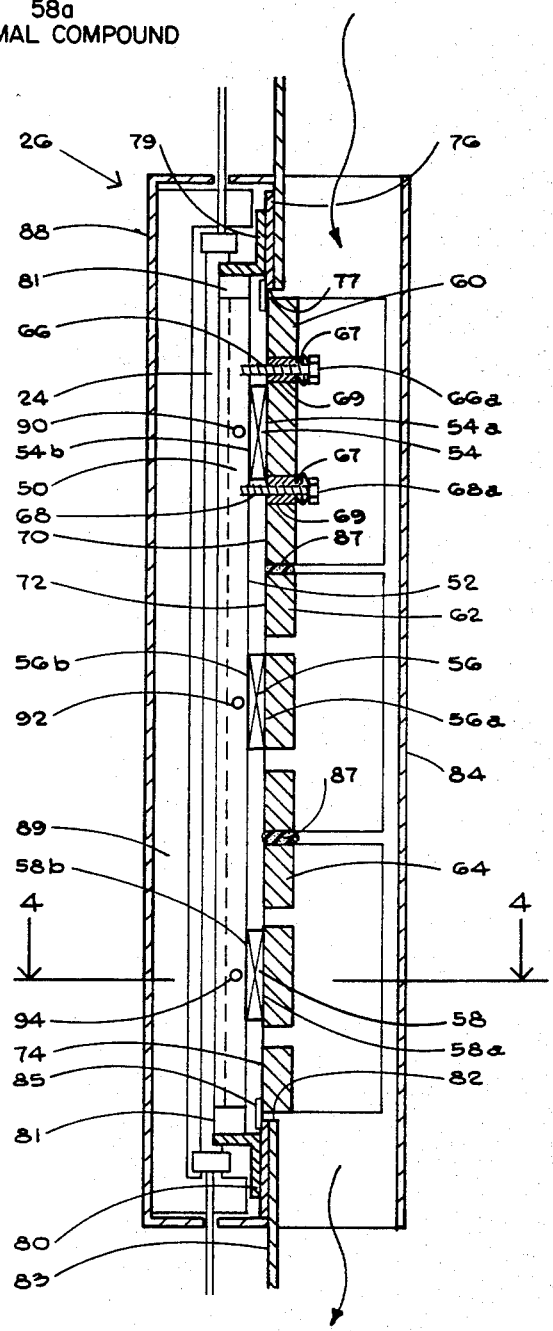

ANALYTICAL INSTRUMENT THERMOELECTRIC TEMPERATURE REGULATOR

BACKGROUND OF THE INVENTION

The present invention is directed to an automated analyzer instrument and, more specifically, is directed to a temperature regulator assembly for an analyzer system such as in chromatography.

For example, in some amino acid analyzers, a very small or micro chromatographic column is used as a specialized application of a liquid column chromatographic separation technique, utilizing ion exchange resin as the stationary phase and eluting buffers of varying pH and salt concentration as the moving phase. Amino acids contained in a sample are introduced at the top of the column and are separated from each other as they are eluted through the resin bed which comprises the column packing. For amino acid analysis, the method of choice for detecting the amino acids in the effluent stream has been to combine the column effluent with a reagent that is metered into the stream at a flow rate proportional to that of the column eluent. When the reagent combines with the amino acids present in the stream, compounds are formed which, when subjected to further development process can be detected by specific changes in optical properties such as absorption or fluorescence.

One of the classical methods in an amino acid analyzer system is that developed by Spackman and Moore, wherein the reagent used in ninhydrin dissolved in a suitable solvent/buffer solution. Under this process, the column effluent/reagent solution is heated in a reactor to a fixed temperature for a specified period of time. The compounds developed as a result of this process will have specific colors, the intensities of which are proportional to the amounts of compounds contained in the flowing stream. The optical densities of these compounds are measured at specific wavelengths. For any of these systems in which stream blending is utilized as part of a detection process, it is important that the operating temperature of the column be very stable. In other words, short-term variations in temperature must be negligible. This is due to the fact that the thermal coefficients of the column and its packing material cause the internal void areas in the column to vary with temperature. In a constant flow system the column which is inserted between the buffer source and the stream blending tee becomes a variable element whose volume is temperature dependent. Variations in temperature are then translated into variations in flow rate of a column effluent. This, in turn, affects the stream blending ratio, which appears as a fluctuation in the analyzer base line.

For use in a micro column amino acid analyzer, this basic system can be automated to analyze samples which are automatically injected into the chromatographic column in a cyclic or repetitive manner wherein the physical conditions of temperature and flow rate are repeated with close precision. The temperature of the chromatographic column is critical to the exchange rate of ions between the liquid phase and the resin bed. Column temperature must be maintained or varied in precisely determined patterns in order to obtain calibration repeatability in an automated amino acid analyzer. Generally, during an analytical procedure, the temperature is increased from a starting level to an elevated end value in a predetermined manner. In automatic analysis it is important that the temperature be returned to stable initial conditions as rapidly as possible in order to minimize the recycle time of the instrument. Under some conditions it is necessary for the starting column temperature to be lower than ambient which requires that the column be cooled. Consequently, it is important that a temperature regulating system for use on the chromatographic column be capable of not only precisely controlling the temperature during the analysis, but also regulating the temperature as rapidly as possible over a wide range of values.

In most prior systems, the temperature of the chromatographic column has been regulated by utilizing some type of liquid bath surrounding the column wherein the temperature of the bath is controlled which in turn controls the column temperature. In this type of system, the thermal inertia of the water makes it relatively easy to limit the previously mentioned short-term cyclic temperature variations. However, this type of system does not provide the requisite speed in regulating the temperature of the column. The use of some type of liquid bath around the column requires additional plumbing and space for the system which is not only more expensive, but also can lead to additional maintenance problems. In addition, the use of a liquid or water jacket surrounding the column to thermostat the temperature can require a considerable amount of power to obtain a relatively slow heating rate. A typical system can require as much as 750 watts to obtain a heating rate of 1° C. per minute. The operation of a liquid bath is such that the rapid cooling from the elevated temperature is provided by immersing a coil within the bath through which cold water is circulated as required.

Another approach which has been used for controlling the temperature of a column is to attach the column to some type of thermally conductive block having electrical resistance heating elements. The cooling required is provided by blowing ambient air across the block. The problem with these arrangements is that their operation is limited to temperatures above ambient.

SUMMARY OF THE INVENTION

The present invention is directed to a temperature regulator system used to control temperature of a fluid stream in a precise and accurate manner with any of numerous types of analytical systems designed for investigation of the chemical constituents of the fluid stream. One such use would be in chromatography such as for a column chromatographic device in an amino acid analyzer, wherein the column is mounted on some type of casing or block to which are attached a plurality of thermoelectric modules that are controlled in such a manner to provide the desired heating and cooling of the column in the amino acid analysis operation. In addition, a heat sink is attached to the thermoelectric elements in order to promote not only the heating by drawing heat from ambient air, but also cooling by exiting heat into ambient air when required.

The control system for the temperature regulator of the column is such that, once a control temperature reference is manually set into the system, a common reference signal is directed to individual power controls for each thermoelectric unit. Also, independent feedback systems are used for each thermoelectric module. These feedback signals are compared with the reference signal to enable adjustment of the temperature of the individual thermoelectric modules to the desired reference temperature. This continuous temperature feedback monitoring and adjustment by each of the respective control systems will provide for the desired temperature regulation throughout the length of the chromatographic column. The thermoelectric modules are operated in a bidirectional mode to provide heating and cooling of the column.

The present invention has greater capability of rapid response, both in heating and cooling, compared to prior systems. In so doing, it still maintains extremely stable temperature control with negligible short-term variation. Further, the system is designed so that it can operate above and below ambient temperature and operates with a significantly faster rate of 12°-15° C. per minute in both heating and cooling.

The utilization of the present invention constitutes a substantially smaller system than a system employing a circulating bath configuration. The present invention requires no plumbing for circulating lines, eliminating the requirement for tap water and a drain for the cooling system or coil. Further, the power consumption of the present invention is approximately one tenth of what is required for the typically utilized liquid bath systems.

The present invention provides an all electric temperature regulator with no moving parts with a capability of rapid recovery to reduce the cycle time during repetitive analyses operation.

BRIEF DESCRIPTION OF THE DRAWINGS

FIG. 2 is a sectional side view of the temperature regulator for the chromatographic column;

FIG. 3 is a front elevation view of the chromatographic column temperature regulator;

FIG. 4 is a sectional view taken along the lines 4—4 in FIG. 2;

DETAILED DESCRIPTION OF THE INVENTION

For exemplary purposes, the application of the present invention will be discussed with respect to its use in an amino acid analyzer system. In such a system it is necessary to accurately control the temperature of the chromatographic column to provide the required exchange rate of ions between the liquid phase and the resin bed.

Figure 1:
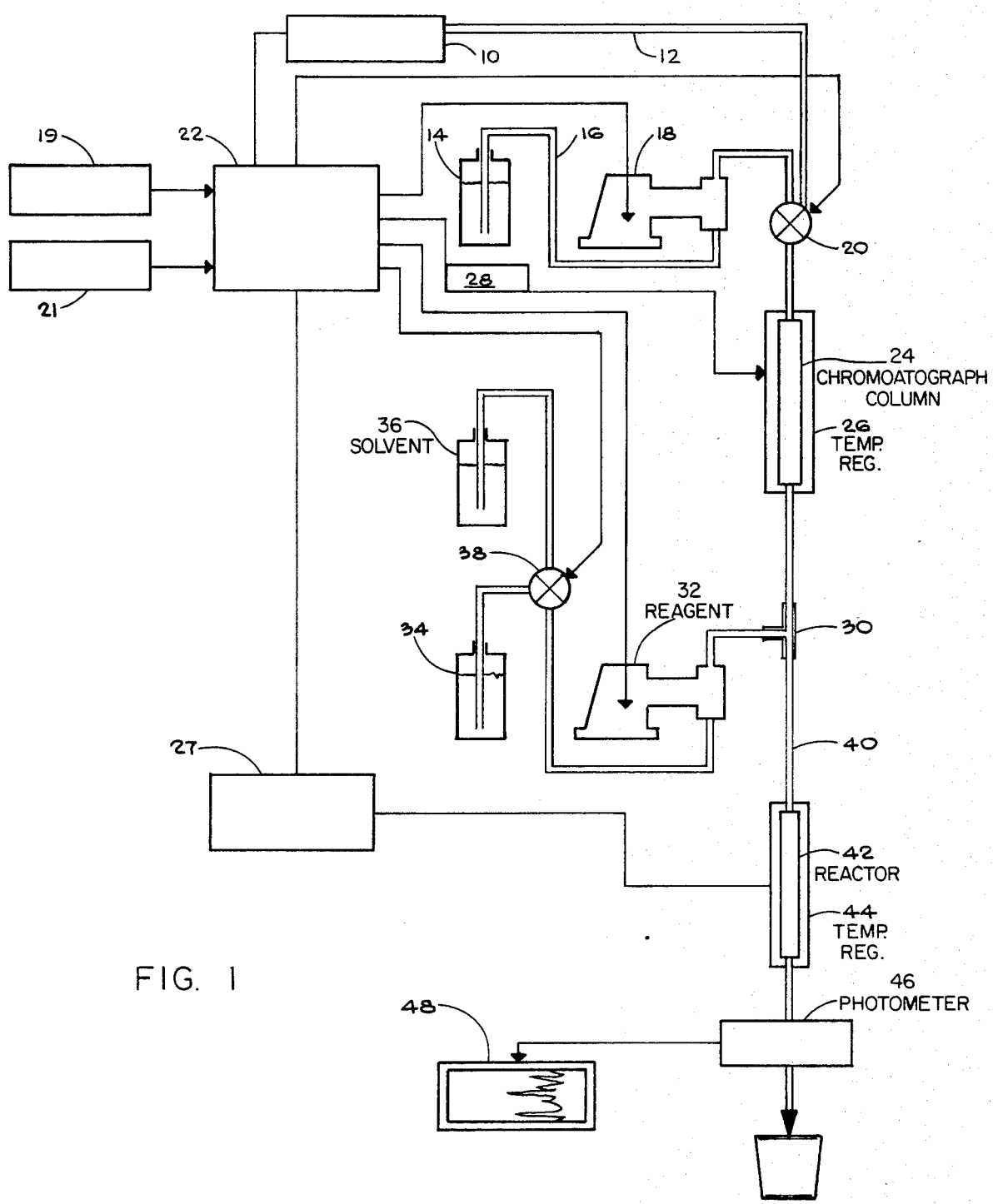
FIG. 1 is a schematic diagram of an amino acid analyzer system.

Attention is directed to FIG. 1, showing a schematic view of an amino acid analyzer system. A sample table 10 receives the various samples for introduction into the automated system which are sequenced through the conduit 12 to the sample injector valve 20. An eluting buffer 14 is transferred through the conduit 16 by the buffer pump 18 into the sample injector valve 20. The sample injector valve 20 is automatically operated by analyzer controller 22 in order to sequence the sample in conjunction with the eluting buffer for introduction into the chromatographic column 24. As explained previously in the Background of the Invention, the liquid column chromatographic separation technique uses an ion exchange resin as a stationary phase with eluting buffers of varying pH and salt concentration as the moving phase. The resin base is packed into the column 24 which establishes a flow path for receipt of the eluting buffer in conjunction with the sample. Attention is also directed to the fact that the column 24 has a temperature regulator assembly 26 comprised of a thermoconductive block, thermoelectric modules and a series of heat sinks to regulate the temperature in the column 24. A control system 28 is utilized to regulate the temperature in the column 24.

After the eluting stream exits the bottom of the column 24, it enters into a mixing tee 30 which is in fluid communication with a reagent pump 32 that is designed to pump the reagent 34 into the mixing tee 30. A solvent 36 is also used by operation of the valve 38 to pump solvent into the system which is done during shutdown procedures.

The mixture of the reagent and the eluting stream from the liquid chromatographic column 24 flows through the conduit 40 into the reaction chamber 42. The compounds produced by the reagent mixing with the amino acids are subjected to further development in the reaction chamber where the mixed flowing stream is heated to a specific temperature for a specific time by a reactor temperature regulator 44. This enhances the ability to detect the presence of these compounds by noting specific changes in optical properties of the stream. The optical density at specific wavelengths will indicate the amounts of compounds present in the flowing stream. A photometer 46 is used to observe these colors and intensities while the recorder 48 provides a documented record.

FIG. 2 shows in more detail the liquid column 24 with its temperature regulator assembly 26. The column 24 is mounted on a column bar or thermoconductive block 50 with a clamp 51 shown in FIG. 4 in such a manner to provide good thermal conductivity between the column 24 and the block 50. The clamp 51 extends substantially the entire longitudinal length of the block 50. The rear face 52 of the thermal block 50 is ground flat and polished to provide a good thermal junction between the thermal block 50 and a plurality of three identical thermoelectric devices 54, 56 and 58 that are in face-to-face contact with the rear surface 52 of the thermal block 50. Depending upon the length of the column 24 and the thermal block 50, it is feasible to construct the temperature regulator assembly 26 with only two thermoelectric devices.

The three thermoelectric elements 54, 56 and 58 are held in compression between the thermal block 50 and three separate respective heat sinks 60, 62 and 64 by two mounting studs 66 and 68 for each of the heat sinks. Each of the studs is threaded to receive tightening nuts 66a and 68a. Included on the studs are a set of compression washers 67 which supply a calibrated force to the thermoelectric devices when the arrangement is assembled. The front surfaces 70, 72 and 74 of the respective heat sinks 60, 62 and 64 are ground flat and polished to provide a good thermal connection or junction between thermoelectric elements and the heat sinks. The studs 66 and 68 for each of the heat sinks are thermally insulated from the heat sinks by insulating sleeves 69. Further, these studs 66 and 68 are preferably made of low conductivity stainless steel. This arrangement will provide for restriction in the heat loss between the thermal block 50 and the heat sinks. In the assembly of the system, a thermal compound is applied to the respective faces 54a, 54b, 56a, 56b, 58a and 58b of the thermoelectric elements 54, 56, and 58 in order to provide good thermal junctions with not only the thermal block 50, but also the separate heat sinks 60, 62 and 64.

The assembly of the thermal block 50, thermoelectric elements 54, 56 and 58 and the heat sinks 60, 62 and 64 is positioned on a mounting plate 76 having an opening 77 to receive the front central portion of each of the heat sinks. The ends of the thermal block 50 are attached to respective mounting brackets 79 and 80 by two stainless steel screws (not shown) which pass through insulating spacers 81. The mounting brackets are secured to the mounting plate 76. A large opening 82 is located in the support wall 83 of the system into which the enlarged or rear side of the heat sinks are inserted. The mounting plate 76 is secured to the support wall 83. This approach for support of the assembly removes all lateral stresses from the thermoelectric elements 60, 62 and 64 so that they are only in compression.

The rear side of the heat sinks are enclosed by the attachment of the plenum 84 to the support wall 83 of the instrument. It should be noted that air is drawn through the plenum by a fan which is not shown. In circumstances when the heat sinks 60, 62, and 64 become cooler than the ambient temperature, the circulated air through the plenum prevents condensation on the heat sinks. The leakage or introduction of air to the column side of the mounting plate 76 is prevented by the placement of a flexible seal 85 around the opening between plate 76 and the heat sinks. In addition, as shown in FIG. 2, urethane foam gaskets 87 are positioned in the separation between the center heat sink 62 and the upper and lower heat sinks 60 and 64. Also, a thermally insulated cover 88 is placed around the thermal block assembly and has insulation 89 to provide thermal isolation from ambient air.

The temperature of the thermal block 50 is monitored by three respective thermistors 90, 92 and 94. These thermistors are located in wells or cavities in the thermal block 50 and are adjacent to the geometric center of each of the thermoelectric elements 54, 56 and 58. Reference is made to FIG. 3 showing the front view of the temperature control assembly 26 for the chromatographic column 24. It should be noted that the size of the individual heat sinks 60, 62 and 64 extend beyond the size of the thermal block 50 and the respective thermoelectric elements 54, 56 and 58. The heat sink 64 is shown in more detail in FIG. 4 having a plurality of heat exchange fins 96 which are located within the plenum chamber 84 for receipt of air for the exchange of heat for the cooling or the heating of the thermal block 50 and the liquid chromatographic column 24.

Figure 7:
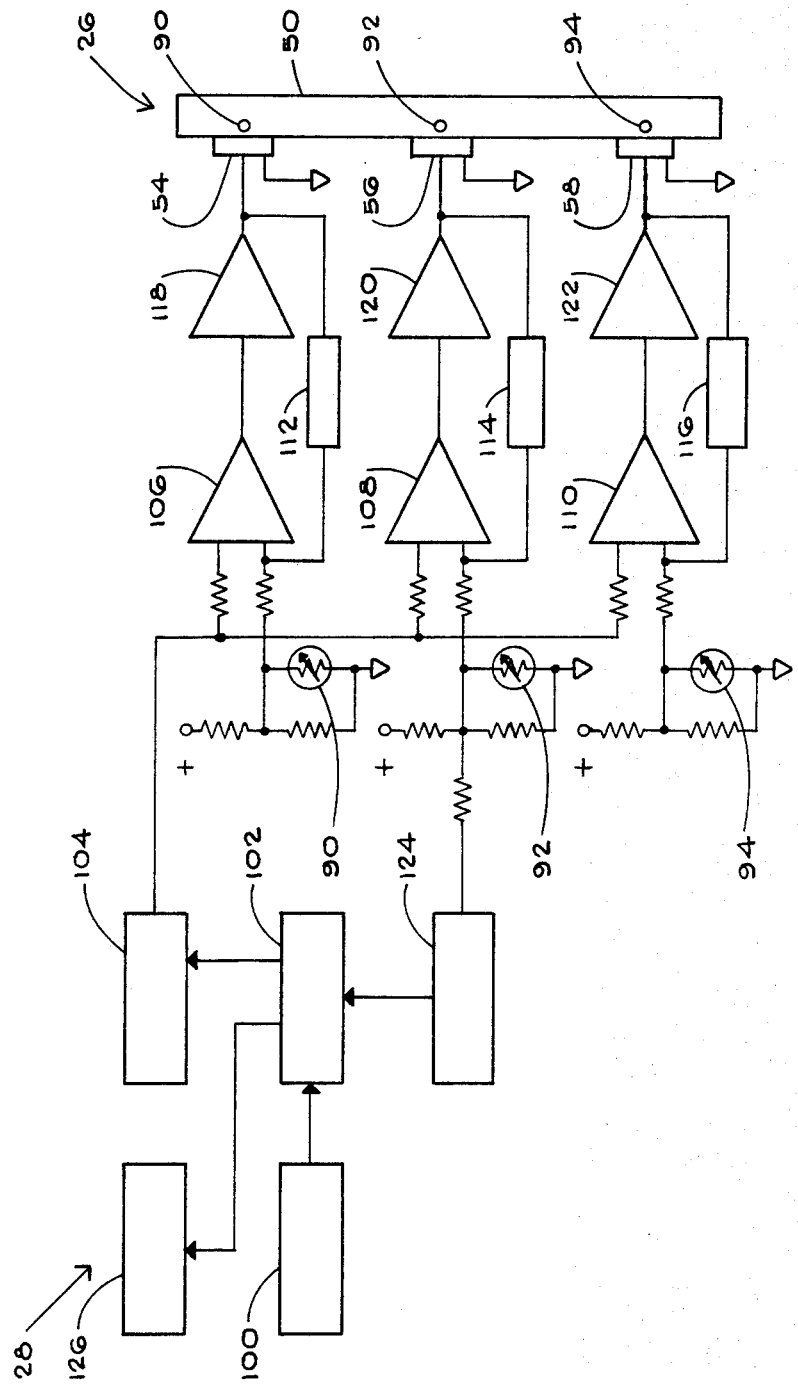
FIG. 7 is a schematic of the control system for the temperature regulator of the present invention.

In FIG. 7 a more detailed schematic is shown with respect to the control system 28 for the thermal regulator assembly 26 of the chromatographic column. A manual digital set is introduced through a control setting 100 into a microprocessor based controller 102. The controller 102 provides a digital input from the control setting to a D/A converter 104 which is designed to convert this value into an analog reference value that is used in conjunction with the three operational or comparative amplifiers 106, 108 and 110 for each of the three respective thermoelectric modules 54, 56 and 58.

The thermistors 90, 92 and 94 are located centrally to each of the respective thermoelectric elements 54, 56 and 58. These thermistors are designed to monitor the temperature of the thermal block 50 and the output of each of these thermistors will provide a signal corresponding to the temperature of the section of the block to which it is attached. The local feedback elements 112, 114 and 116 provide dynamic stability to the control system. The reference signal will be compared with the feedback signal and the difference will be adjusted in the output from the operational amplifiers 106, 108 and 110 to their respective power amplifiers 118, 120 and 122 for adjusting the amount of power input to the respective thermoelectric elements 54, 56 and 58. It should be noted that the amplifier networks have directional outputs. Current flowing in one direction in the thermoelectric elements will cause the block 50 to cool, while current flowing in the reverse direction will cause the block to heat.

The output of the center thermistor 92 provides analog signal to the controller 102. This signal is converted to an appropriate digital format by an A/D converter 124 and fed back into the controller. The controller continuously compares this value to the reference or control set 100, so that it can adjust its output to D/A converter 104 to cause the digital value of the signal from the thermistor 92 to equal value of the digital set point. The controller 102 also outputs the digital value of the signal from the thermistor 92 to a digital display 126. Therefore, it can be seen that the controller 102 in operation of the overall control system functions to adjust the temperature of the thermal block 50 and the column 24 until the digital value of the temperature appearing in the display 126 matches the desired control set 100. In the actual use of the amino acid analyzer system the control set point 100 may be set manually by the operator or it may be automatically controlled in response to a program entered by the operator during automatic operation.

Figure 5:
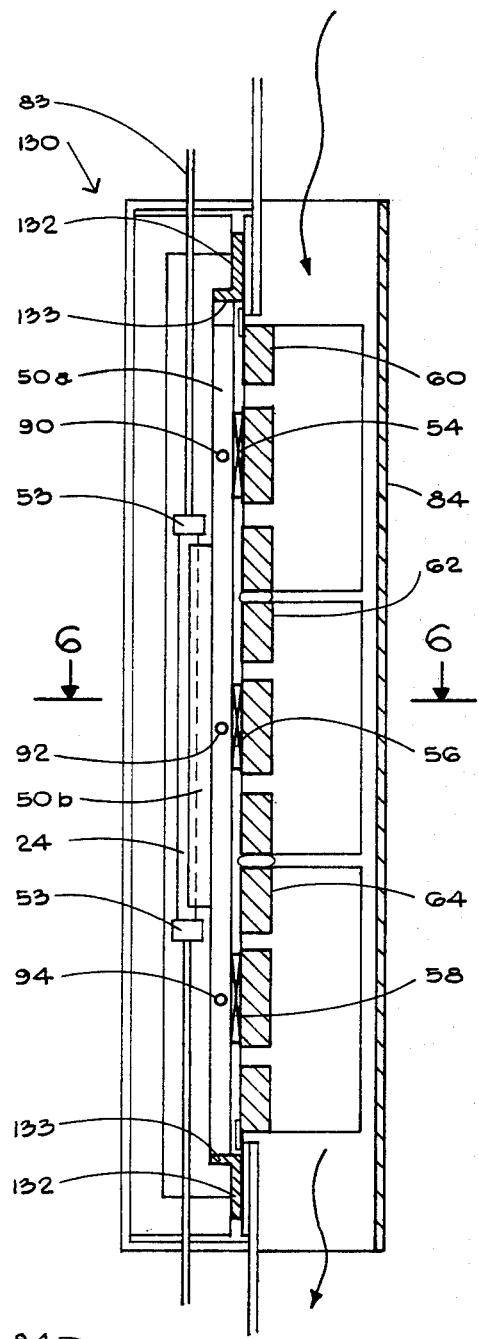
FIG. 5 is a sectional side view of the temperature regulator adapted to receive a shorter column.
Figure 6:
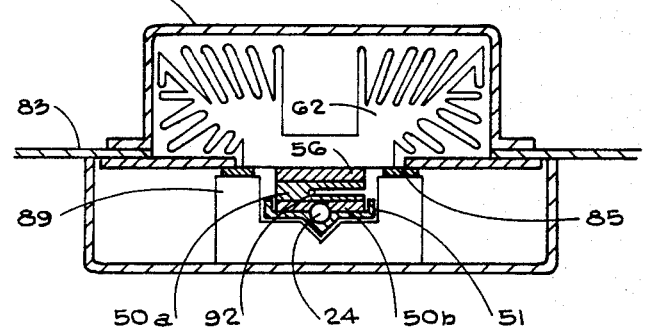
FIG. 6 is a sectional view taken along the lines 6—6 in FIG. 5.

In a preferable embodiment 130 of the present invention the thermal block 50 is made from two separate longitudinal pieces, the thermal section 50a and the holder section 50b as shown in FIGS. 5 and 6. The thermal section 50a is designed for direct thermal contact with the thermoelectric devices 54, 56 and 58 in the manner described above. The thermal section 50a is held by L-shaped brackets 132 which have a shorter ledge portion 133 than the brackets 79 and 80 for the embodiment shown in FIG. 2. The holder section 50b is designed in such a manner that its interior face adjacent the thermal section 50a is ground smooth and polished to mate with and connect to the front smooth and polished surface of the thermal section 50a. Thermal conductive material is utilized between the two sections to create a good thermal path between the two sections. The holder portion or section 50b is designed to support the column 24.

As shown in FIG. 5, a shorter holder section 50b can be utilized to support varying length columns 24. Column end fittings 53 are larger than the diameter of the column 24 itself and have a hexagonal shape. Hence, they cannot be included within the heat transfer junction between column 24 and holder 50b. Holder 50b permits column 24 to be clamped securely while the end fittings extend beyond the holder 50b. This permits columns of shorter length to be mounted to thermal plate 50a. Attachment means such as machine screws are utilized for securing the holder section 50b to the thermal section 50a. The remainder of the construction of the temperature regulator assembly 130 is the same as the assembly 26 shown in FIGS. 2-4. Hence, the majority of the same reference numbers are used in FIGS. 5 and 6 as in FIGS. 2-4.

It has been found that it is critical and very important to the operation of the thermal regulation described that separate sensing and driving circuits be used for the three thermoelectric elements. This is necessary because of the characteristics of the thermoelectric elements as well as the physical geometry of the liquid chromatographic column itself.

In order to obtain good thermal contact between thermoelectric elements or modules and the apparatus which they are heating or cooling, it is necessary that the surfaces of the thermoelectric elements be flat and essentially parallel. However, multiple thermoelectric devices are needed to cover the entire length of a long, flat surfaced thermal block which is holding an item such as a chromatographic column. Because multiple thermoelectric devices are utilized with respect to the geometry of the long, thin shape of the chromatographic column, a problem arises with respect to the interface of the heat sink to multiple thermoelectric units. Since the thermoelectric units may not be made to have the same thickness from unit to unit without extreme expense, it is extremely difficult to have a single heat sink properly attached to the surface of three adjacently positioned thermoelectric units. Certain gaps may exist which would not allow for the good thermal junction necessary between the heat sink and the thermoelectric units. Consequently, the concept of using a separate heat sink for each thermoelectric unit is utilized.

Because each thermoelectric unit has its own characteristic heat pumping coefficient which varies from unit to unit, a common current introduced into all thermoelectric units would result in different energy being transmitted across each. It then becomes necessary to provide individual control circuits for each thermoelectric unit in order to compensate for the differences in the heat pumping coefficients.

If a system were to comprise a single controller for a plurality of these thermoelectric elements, there would be a resultant temperature gradient of several degrees along the column. The use of individual control loops in the electronic control can significantly limit the temperature gradient to within one tenth of a degree, and the system will stabilize in less than one minute. The use of the microprocessor in the reference control loop is to permit the digital set point entry and the digital temperature display with no variation between the set point and the actual displayed value. In addition, the nonlinear characteristics of the thermistor bridge output can be compensated by a routine in the controller as it generates the digital reference signal for the D/A converter.

It has been found in the use of the present system that the following performance is possible in the regulation of the temperature for the chromatographic column:
Temperature Span: 0.0° to 90.0° C.
Heating Rate: (50° C. to 65° C.) 12° C. per minute
Cooling Rate: (65° C. to 50° C.) 15° C. per minute
Short Term Cycling, peak to peak: 0.02° C.
Long Term Stability, within +or−0.1° C.
Absolute Set Point Accuracy, within +or−0.5° C.
Ambient Temperature Range: 10° C. to 43° C.
Power Consumption: 50 watts It should be noted that the above discussed temperature regulating assembly for the liquid chromatographic column is not necessarily limited to such a specific use.

The present arrangement can be used to precisely and accurately control the temperature of a fluid stream in any analytical system designed for investigation of the chemical constituents of the fluid stream. Any process which would require the rapid heating and cooling of a particular element that is mounted on a conductive wall and requiring the heating capacities within the range of the capabilities of thermoelectric modules could utilize the present system. The accommodation of various physical aspect ratios by the use of independent thermal control loops adds to the versatility of the present system. It should be noted that the manner in which the reference signal is generated could be an analog system instead of the digital approach which is utilized in the present system described above.

What is claimed is:

1. A temperature regulator assembly for use in an analytical device comprising:
    (a) an elongated column;
    (b) thermally conductive support means for supporting said column;
    (c) at least one heat sink;
    (d) a plurality of thermoelectric devices connected to said support means and to said heat sink for conducting heat therebetween and thereby heating or cooling said column;
    (e) a plurality of temperature sensing elements connected in temperature sensing relationship to respective parts of said column; and
    (f) control means responsive to said sensing elements for controlling said plurality of thermoelectric devices to maintain a uniform temperature along said column, said control means acts in conjunction with individual control circuits connected to respective temperature sensing elements and respective thermoelectric devices.

2. The temperature regulator assembly of claim 1 in which the column is a chromatographic column.

3. The temperature regulator assembly of claim 1 wherein said support means extends over a relatively large fraction of the length of the column.

4. The temperature regulator assembly of claim 1 wherein the support means comprises:
    (a) a thermal contact portion for attachment to the heat sink; and
    (b) a holder portion for receipt of the column, the contact portion and the holder portion being in direct thermal communication.

5. The temperature regulator assembly of claim 4 in which the holder portion is replaceably connected to the contact portion so that the holder portion can be adjusted to accommodate columns of different sizes.

6. The temperature regulator assembly of claim 1, including a plurality of heat sinks, in which each thermoelectric device is connected to a respective heat sink.

7. The temperature regulator of claim 1, including means for generating a temperature reference signal, in which each control circuit includes comparing means having a first input connected to the respective temperature sensing element, a second input connected to receive the temperature reference signal, and an output connected to the respective thermoelectric device.

8. The temperature regulator assembly of claim 1 including an air flow duct for conducting a flow of air over the heat sink.

9. The temperature regulator assembly of claim 8 including a fan for blowing air through said duct.

* * * * *